United States Patent
Jess et al.

(10) Patent No.: US 10,859,804 B2
(45) Date of Patent: Dec. 8, 2020

(54) COMBINATION OF OPERATING MICROSCOPE AND ENDOSCOPE

(71) Applicant: Carl Zeiss Meditec AG, Jena (DE)

(72) Inventors: Helge Jess, Oberkochen (DE); Martin Fanenbruck, Oberkochen (DE); Roland Guckler, Ulm (DE)

(73) Assignee: Carl Zeiss Meditec AG, Jena (DE)

( * ) Notice: Subject to any disclaimer, the term of this patent is extended or adjusted under 35 U.S.C. 154(b) by 148 days.

(21) Appl. No.: 15/954,594

(22) Filed: Apr. 16, 2018

(65) Prior Publication Data
US 2018/0307023 A1 Oct. 25, 2018

(30) Foreign Application Priority Data
Apr. 19, 2017 (DE) .................. 10 2017 206 561

(51) Int. Cl.
| | |
|---|---|
| G02B 21/06 | (2006.01) |
| G02B 23/24 | (2006.01) |
| G02B 21/36 | (2006.01) |
| A61B 90/20 | (2016.01) |
| A61B 1/00 | (2006.01) |

(Continued)

(52) U.S. Cl.
CPC .......... *G02B 21/06* (2013.01); *A61B 1/00108* (2013.01); *A61B 1/0646* (2013.01); *A61B 1/0684* (2013.01); *A61B 90/20* (2016.02); *G02B 21/0012* (2013.01); *G02B 21/082* (2013.01); *G02B 21/36* (2013.01); *G02B 21/361* (2013.01); *G02B 23/2461* (2013.01);

(Continued)

(58) Field of Classification Search
None
See application file for complete search history.

(56) References Cited

U.S. PATENT DOCUMENTS 5,408,263 A * 4/1995 Kikuchi ............. A61B 1/00059
348/223.1
9,829,692 B2 11/2017 Reimer et al.
(Continued)

FOREIGN PATENT DOCUMENTS

| DE | 102009017710 A1 | 10/2010 |
|---|---|---|
| EP | 928981 A2 | 7/1999 |

OTHER PUBLICATIONS

Office Action issued in German Patent Application No. DE 10 2017 206 561.3 (from which this application claims priority), dated Sep. 20, 2017 and English language machine translation thereof.
(Continued)

*Primary Examiner* — Derek S. Chapel
(74) *Attorney, Agent, or Firm* — Falk Ewers; Ewers IP Law PLLC

(57) ABSTRACT

A system combines an operating microscope and an endoscope. The operating microscope includes a light source with a first color temperature that illuminates a first portion of an operating field. The endoscope includes an LED light source with a second color temperature that illuminates a second portion of the operating field, wherein the two color temperatures are matched to one another in such a way that, in optical and/or digital imaging of the operating microscope and/or in optical and/or digital imaging of the endoscope, there are no perceivable color differences in portions of the operating field that are illuminated and observed jointly by the operating microscope and the endoscope.

18 Claims, 5 Drawing Sheets

(51) Int. Cl.
    *A61B 1/06*     (2006.01)
    *G02B 21/00*     (2006.01)
    *A61B 90/30*     (2016.01)
    *G02B 21/08*     (2006.01)
    *H01J 61/16*     (2006.01)

(52) U.S. Cl.
    CPC .......... *G02B 23/2484* (2013.01); *H01J 61/16* (2013.01); *A61B 2090/309* (2016.02)

(56) References Cited

U.S. PATENT DOCUMENTS

| | | | | |
|---|---|---|---|---|
| 2005/0099824 A1* | 5/2005 | Dowling | .............. | A61B 1/0653 |
| | | | | 362/572 |
| 2010/0056928 A1* | 3/2010 | Zuzak | ................. | A61B 5/0071 |
| | | | | 600/476 |
| 2010/0261966 A1* | 10/2010 | Reimer | ................. | A61B 90/30 |
| | | | | 600/160 |
| 2011/0234782 A1* | 9/2011 | Ehrhardt | ................ | A61B 1/063 |
| | | | | 348/68 |
| 2012/0010465 A1* | 1/2012 | Erikawa | ................. | A61B 1/05 |
| | | | | 600/109 |

OTHER PUBLICATIONS

DIN Standard DIN 6169, Part 1 (Jan. 1976) and Part 2 (Feb. 1976) and English language translation thereof.

\* cited by examiner

COMBINATION OF OPERATING MICROSCOPE AND ENDOSCOPE

CROSS REFERENCE TO RELATED APPLICATIONS

This application claims priority to German patent application DE 10 2017 206 561.3, filed Apr. 19, 2017, the entire content of which is incorporated herein by reference.

TECHNICAL FIELD

The invention relates to a combination of an operating microscope and an endoscope, which are each equipped with a dedicated light source and which are used together in a surgical intervention.

BACKGROUND

By way of example, operating microscopes are known from the "PENTERO" product line by the applicant. Using an operating microscope, it is possible to present, in a magnified form, an operating field on a patient to be operated on by a monocular, typically binocular, observation beam path. To this end, the operating microscope has eyepieces, lenses and a magnification optical unit with, in particular, variable magnification in order to image the operating field in a magnified manner for a treating physician. By way of example, operating microscopes are arranged at a wall, ceiling or stand and can typically be moved and/or pivoted in all spatial directions in order to facilitate the respectively desired view of the operating field.

Furthermore, an additional observation beam path, for example for an assistant and/or an image recording apparatus and/or a data superimposition device and/or an apparatus for optical coherence tomography and/or a mechanical or optical (laser) treatment apparatus, may be provided on the operating microscope.

A light source is assigned to the operating microscope for the purposes of illuminating the operating field. Depending on the preferences of the treating physician, the light source conventionally includes a xenon or a halogen light source, i.e., gas-discharge lamps with the respective elements for producing light, or, by now, an LED light source as well. It is known that xenon and halogen lamps respectively have different color temperatures, i.e., cause different color impressions, at least subjectively, at the treating physician through the observation beam paths of the operating microscope in each case.

Furthermore, endoscopes are known for micro-invasive interventions on a patient, for example. The endoscopes likewise include an observation beam path with, for example, eyepiece, lens and magnification optics and a light source for illuminating an operating field. Furthermore, provision can be made of, e.g., mechanical means for treatment or specimen removal, or else of means for optical or electromagnetic manipulation, that is to say, for example, for electrical obliteration or heat treatment. So-called static endoscopes include an external light source such as likewise a xenon light source, for example.

Particularly flexible or manual endoscopes or endoscopes held in the hand of a treating physician are equipped with a light source having an LED (light-emitting diode). Here too, the use of fiber optics for reducing the installation size is known. The light source is arranged in a handpiece of the endoscope. There is a digital image capture in such handheld endoscopes. This means that there is no eyepiece for looking through but, instead, the image of the operating field captured by the lens system of the endoscope is captured by a CCD chip, for example, and directly presented on a monitor and/or recorded.

Finally, the use in a surgical intervention of both an operating microscope and an endoscope as a combination by a treating physician, or together with an assistant, is known. By way of example, the actual operating field can be seen by the operating microscope in the case of a cerebrosurgical intervention. At the same time, the operating field or surrounding tissue such as arteries or a cavity can be seen, as it were, from the side or from behind by the endoscope to provide the treating physician with more information.

Here, with its light source, e.g., a xenon light source, the operating microscope illuminates a first portion of the operating field; and a second portion of the operating field is illuminated by the light source of the endoscope. These two portions may overlap, at least in part. Thus, there is a common illumination by the light source of the operating microscope and by the light source of the endoscope in this overlap region of the two portions. The overlap region is observed by the operating microscope and by the endoscope or, for example, in the case of the endoscope, imaged on a monitor. However, an effect occurring here is that a change in the color impression when observing the operating field with the operating microscope may be caused by the endoscope with the LED light source, at least in the portion of the operating field that is illuminated together by the two light sources. There may be a color change when observing the operating field by the operating microscope, for example, since there is a difference in the color temperatures of the two light sources or the color rendering indices of operating microscope and endoscope. By way of example, if the operating microscope is equipped with a xenon light source that has a relatively uniform intensity distribution in the color spectrum over the range visible to the human eye, and the endoscope is equipped with a white light LED that has a typical peak in the blue spectral range, there is a color change in the optical rendering of the operating microscope as a result of the light source of the endoscope. The light of the endoscope is perceived as too cold in relation to the color temperature or the image perceived through the operating microscope by the treating physician is perceived as red-tinged, at least in portions. Here, the adjective "red-tinged" should be understood in such a way that, at least subjectively, a color temperature that is too warm or a different color in the CIE (1931) color space is discerned or perceived. Objectively, a white balance of a camera, for example of the operating microscope, exhibits a color deviation in the region of an operating field that is illuminated together by the endoscope and operating microscope, or their respective light sources, and respectively observed accordingly. As a result of this modified perception, an assessment of the treating physician, for example in respect of which regions of the operating field have to be manipulated, may be disturbed or impaired.

SUMMARY

In view of the forgoing, a system which combines an operating microscope and an endoscope is improved to realize an observation of the actual operating field that, in particular, is not influenced by the color temperature.

The problem is resolved by providing a system having the features disclosed herein.

A core concept of the invention is the light source of the operating microscope and the LED light source of the endoscope being matched to one another in such a way that, when observing the operating field through the operating microscope, there is no longer a color change as a result of the light source of the endoscope, or at least only a minor color change which, in particular, is no longer perceivable by the human eye. Here, a first portion of the operating field is illuminated by the light source of the operating microscope and a second portion of the operating field is illuminated by the LED light source. This means that the light of both light sources is superimposed in that portion of the operating field that is illuminated by both the light source of the operating microscope and the light source of the endoscope together, i.e., in which the aforementioned first and second portions overlap, but no color change occurs when observing the operating field, in particular by way of the operating microscope, as a result of adapting the LED light source of the endoscope to, e.g., the xenon light source of the operating microscope. Here, this overlap region is observed both by the operating microscope and the endoscope or is observed or seen by a treating physician through the operating microscope and, for example, imaged on a monitor by an endoscope. In particular, this should be understood to mean that no color differences, at least no color differences that can be subjectively perceived by the treating physician, occur in the regions illuminated and observed together by the operating microscope and the endoscope. Objectively, a white balance of a camera, for example of the operating microscope, exhibits a color deviation in the region of an operating field that is illuminated together by the endoscope and operating microscope, or their respective light sources, and respectively observed accordingly, no change. In particular, an LED light source with a higher color temperature is provided for the endoscope, said LED light source being matched to the color spectrum, known per se, of a xenon light source of the operating microscope. This avoids a falsification or change of the color impression of the operating field. This means that a color, or a spectrum locus in the CIE (1931) color space does not change by the additional illumination of the endoscope, or is not perceived by a human observer.

It is understood that both the operating microscope and the endoscope are in each case designed for optical and/or digital image capture. A digital image capture means that, for example in the case of an endoscope, no eyepiece is provided for immediate viewing but that an image is captured, for example by a CCD chip, and the image is directly reproduced on a monitor for a treating physician and/or recorded.

Appropriate LEDs with a color spectrum, or a color temperature, that is matched to a xenon light source are known from the related art. It is also clear that the respective brightness or intensity of the light sources is adjustable as desired.

It is understood that the operating microscope and the endoscope may be actuatable together, or independently of one another, for example in respect of the respective brightness of the light sources. Amongst others, hand or foot switches or a menu-guided control on a monitor serve to this end.

The scope of the invention also includes the use of a combination of operating microscope and a visualization system, arbitrary per se, with a dedicated light source instead of a combination of operating microscope and endoscope. By way of example, this may be a hyperspectral camera with a dedicated light source.

In a typical embodiment, the operating microscope is equipped with a xenon light source and the endoscope is equipped with an LED light source. Here, the color temperature of the LED light source deviates from the color temperature of the xenon light source by at most 500 K. Consequently, a falsification of the color impression perceived by a treating physician, for example through the operating microscope, when an operating field is also illuminated by the endoscope with its LED light source in addition to the illumination by the xenon light source is avoided. This means the treating physician does not perceive a color change despite the additional illumination. Naturally, the same also applies to digital image capture by the operating microscope and/or endoscope, for example. An even better result is obtained if the color temperature of the LED light source deviates by no more than 300 K from the color temperature of the xenon light source; at most 100 K are more typical and 50 K are particularly typical.

It is clear that, in principle, a halogen light source or an LED light source can also be used for the endoscope and then a correspondingly designed LED is used for the endoscope.

An important parameter for describing an illumination apparatus is the color rendering index value and the R9 index value. For each light source or illumination apparatus, the color rendering index value characterizes how well it can render the colors in comparison with sunlight. Here, only colors from the visible wavelength spectrum are considered. The higher the color rendering index value of a light source or illumination apparatus, the more natural the color rendering or the color impression of the object illuminated therewith. The lower the color rendering index value, the more the color impression of an object is falsified by the illumination apparatus. The maximum color rendering index value is 100.

The color rendering index value is calculated according to DIN 6169. DIN 6169 defines 14 test colors with a normalized remission curve. These 14 test colors are R1: Altrosa [antique pink], R2: Senfgelb [mustard yellow], R3: Gelbgrün [yellow green], R4: Hellgrün [light green], R5: Türkisblau [turquoise blue], R6: Himmelblau [sky blue], R7: Asterviolett [aster purple], R8: Fliederviolett [syringa purple], R9: Rot gesättigt [saturated red], R10: Gelb gesättigt [saturated yellow], R11: Grün gesättigt [saturated green], R12: Blau gesättigt [saturated blue], R13: Rosa [pink] (skin tone), R14: Blattgrün [leaf green]. The R9 index value serves as a statistic for the special color rendering index value R9 for the color "9" (saturated red). The maximum R9 index value is 100.

If the five light emission apparatuses are selected in such a way that the five dominant wavelengths lie in the specified wavelength ranges, it is possible to produce white light with a very natural color impression. The color rendering index value has a value in a range from 87 to 100. The R9 index value has a value in a range from 45 to 100. Typically, the color rendering index value has a value in a range from 90 to 100, typically a value in a range from 95 to 100. The R9 index value typically has a value in a range from 60 to 100, more typically in a range from 80 to 100, particularly typically in a range from 87 to 100.

Here, the operating microscope with its light source—xenon, halogen or LED—has a first color rendering index and the endoscope with its light source has a second color rendering index. If these two indices differ by a value of five, a treating physician cannot determine any color change or any change of the color impression in a portion of the operating field that is illuminated by both light sources together. A maximum difference of four of the color rendering indices, better at most three or only two, in particular only one, is particularly typical.

It is proposed that the endoscope is a manually portable endoscope; in particular, the LED light source is integrated therein. By the manually portable endoscope, it is possible, for example, to see the operating field from the side or from behind in order to see arteries, cavities in the tissue or the like. Here, the LED light source is arranged in a handle or gripping piece of the endoscope.

A white light LED is particularly advantageously provided as LED light source of the endoscope to obtain a correspondence that is as large as possible with the color spectrum of the xenon light source of the operating microscope. In principle, use can also be made of an RGB LED.

In order to adapt the color spectrum or the color temperature of the light source of the endoscope to the light source of the operating microscope, the endoscope light source can be embodied as an RGB LED. This means that this is a combined LED which is able to emit red, green and blue light. It is understood that the respective light sources are actuatable in respect of their respective intensity in order, overall, to produce light with a desired intensity or brightness and a desired color spectrum or desired spectral distribution or a desired color impression. For special applications, RGB LED light sources could be extended by further LEDs with "additional colors." For example, they could be extended with additional edge peaks or intermediate peaks for a more uniform spectrum illumination for a higher CRI value or color rendering index value, or for example with a deep blue (405 nm) wavelength or a near infrared wavelength (800 nm) for the purposes of exciting fluorescence.

For further improvement of the optical and/or digital imaging of the operating microscope and/or in the case of optical and/or digital imaging of the endoscope, a white balance is provided. In particular, this is effectuated independently by appropriately embodied controller hardware and/or software, and consequently it is possible to set a color temperature of imaging of the operating field to 4000 K, for example. It is understood that a white balance can be effectuated in a camera or recording device of the operating microscope and/or of the endoscope, for example. In principle, this can be effectuated in respect of one of the light sources in an alternative or additional manner.

Various light sources may also be provided for the operating microscope, for example a xenon and a halogen light source, or an LED. These can then be selected by a treating physician, depending on the desired color impression of the operating field. Here, a configuration of the light source of the endoscope as an RGB LED is provided to obtain a corresponding color temperature in a simple manner.

In principle, it is also possible for the color temperature or the color spectrum of the respective other light source to be taken into account within the scope of image processing of the operating microscope and/or the endoscope. This means that if, for example, the operating field is illuminated and observed by a xenon light source of the operating microscope and an endoscope with a light source having a different color temperature illuminates the operating field at the same time, this is taken into account by appropriately designed software or electronics, for example when presenting the operating field by way of the operating microscope, and a corrected color rendering is imaged.

In order to improve a view of the operating field, both light sources of the operating microscope and of the endoscope are typically changeable in terms of their respective color spectrum or their color temperature. Consequently, the respective light sources can be adapted to one another and the rendering of the operating field with color fidelity can be improved. By way of example, RGB LEDs in each case serve to this end.

Additionally, or alternatively, color filters can be in each case assigned to the light sources of the operating microscope and/or endoscope, the color filters, for example, being pivotable out of and into an illumination beam path. Consequently, it is possible to configure a color temperature or a color spectrum as desired.

It goes without saying that the aforementioned features and those yet to be explained below can be used not only in the combination specified in each case but also in other combinations or on their own, without departing from the scope of the present invention.

BRIEF DESCRIPTION OF THE DRAWINGS

The invention will now be described with reference to the drawings wherein.

DESCRIPTION OF EXEMPLARY EMBODIMENTS

Figure 1:
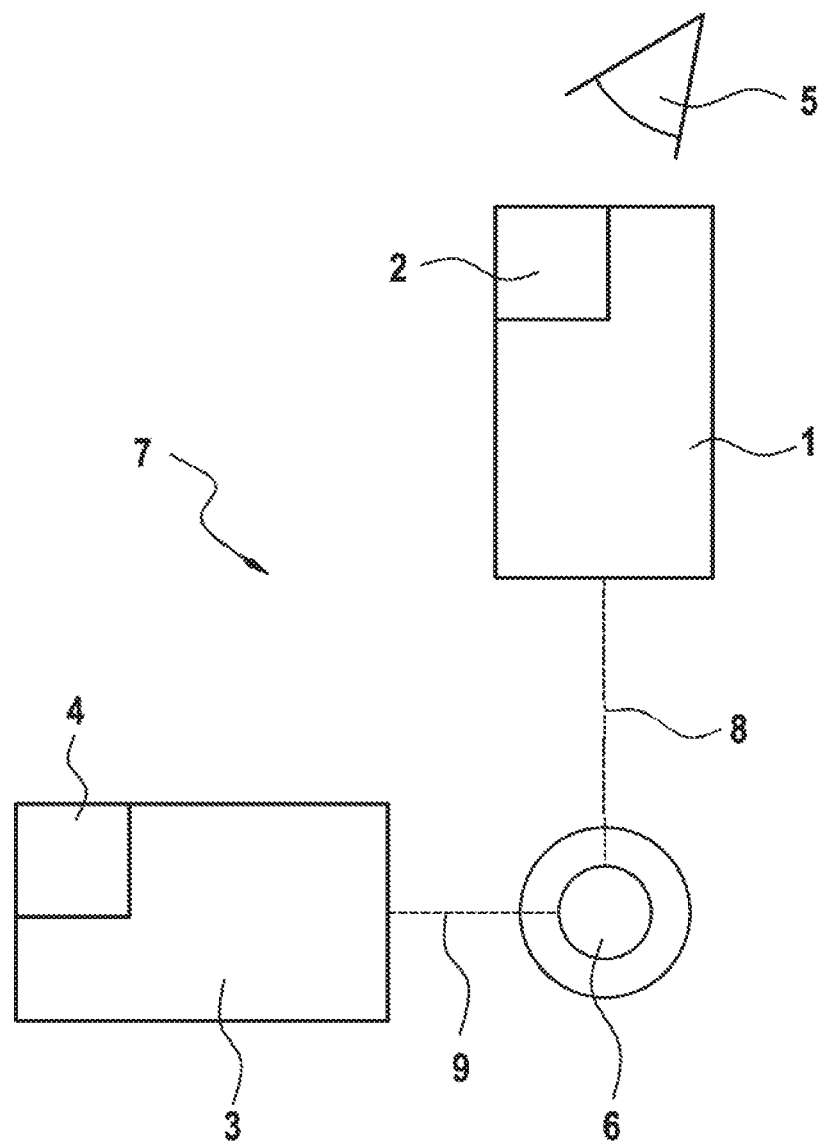
FIG. 1 shows a system combining an operating microscope and an endoscope in a schematic illustration.

The exemplary embodiment illustrated in FIG. 1 is a schematic reproduction of a system 7 combining an operating microscope 1 and an endoscope 3. By way of example, the operating microscope 1 is a model from the "PENTERO" series by the applicant and it is equipped with a xenon light source 2, the spectrum of which is reproduced in FIG. 4. The operating microscope 1 is equipped, in a manner known per se, with eyepieces, objectives or lenses, and with a typical variable magnification optical unit in order to present an operating field 6, such as a region of the brain of a patient to be treated, in a magnified manner to a treating physician 5. The treating physician 5 sees the operating field 6 via an observation beam path 8, which may also have a binocular embodiment. Furthermore, a further observation beam path for an assistant and/or device for image capture and/or data superimposition and/or for optical coherence tomography may be provided on the operating microscope 1.

Figure 3:
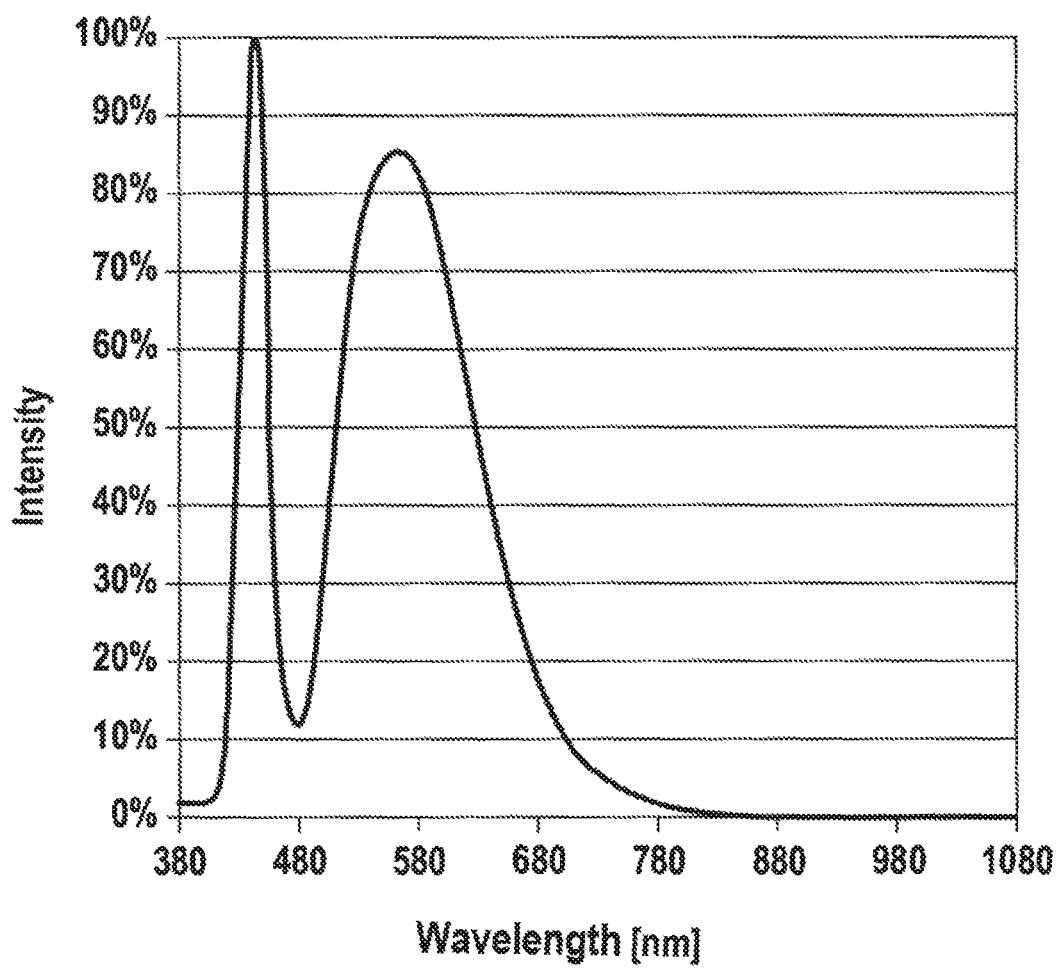
FIG. 3 shows the spectrum of a white light LED light source of an endoscope.

By way of example, the endoscope 3 is the model FSC200 by Schölly Fiberoptic GmbH, Robert Bosch Straße 1-3, 79211 Denzlingen, Germany, and it includes an LED light source 4, the spectrum of which is imaged in FIG. 3. Here, this is a white light LED light source. The operating field 6 can also be seen via the observation beam path 9 by the endoscope 3 by way of a magnification optical unit and, optionally, eyepieces, lenses or objectives. The endoscope 3 may also capture the operating field 6 only digitally and reproduce an image, for example on a monitor. By way of example, the operating field 6 can be seen, as it were, from the top using the operating microscope 1 and the operating field 6 can be seen from the side, for example, by the endoscope 3 so as, inter alia, to look into cavities or to look behind a blood vessel. The endoscope 3 is typically a hand-held endoscope 3, wherein the LED light source 3 is typically arranged in a handle, i.e., outside of a patient body.

It is understood that the operating microscope 1 and/or the endoscope 3 are embodied for optical and/or digital capture of the operating field 6. This means that the operating field 6 can be observed in each case either directly optically through eyepiece and lens, amongst others, and/or cameras are provided in each case for digital image capture.

The operating microscope 1 with its light source 2 illuminates a first portion of the operating field 6 and the endoscope 3 with its LED light source 4 illuminates a second portion of the operating field. At least in a portion of the operating field 6 that is illuminated together and observed by the operating microscope 1 and endoscope 3, the two illuminations are overlaid, and so there may be a modified color perception or a modified color impression through the operating microscope 1, for example.

Figure 2:
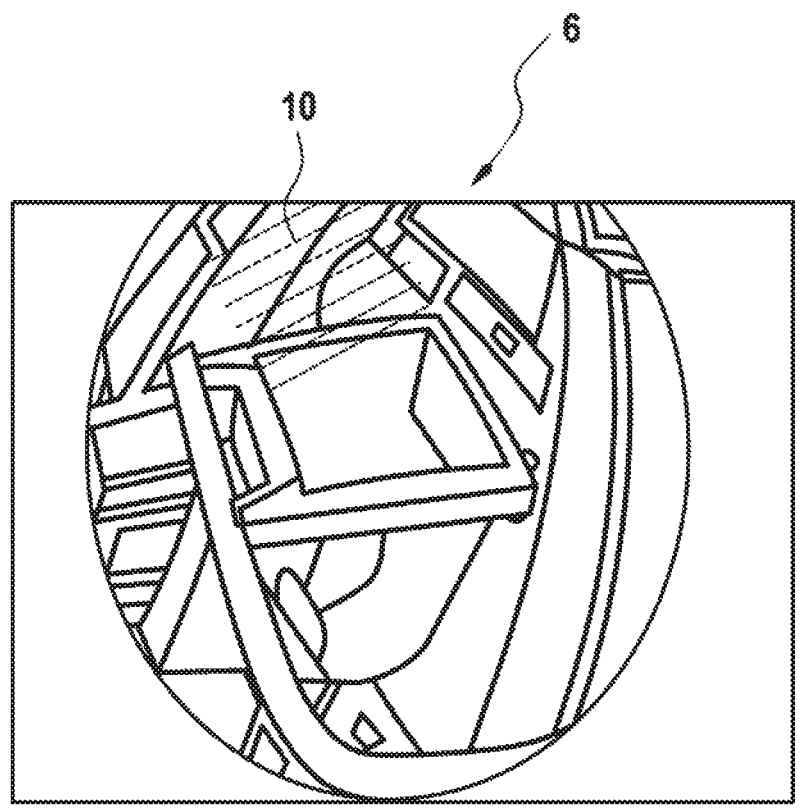
FIG. 2 shows a red-tinged image of an operating field.
Figure 4:
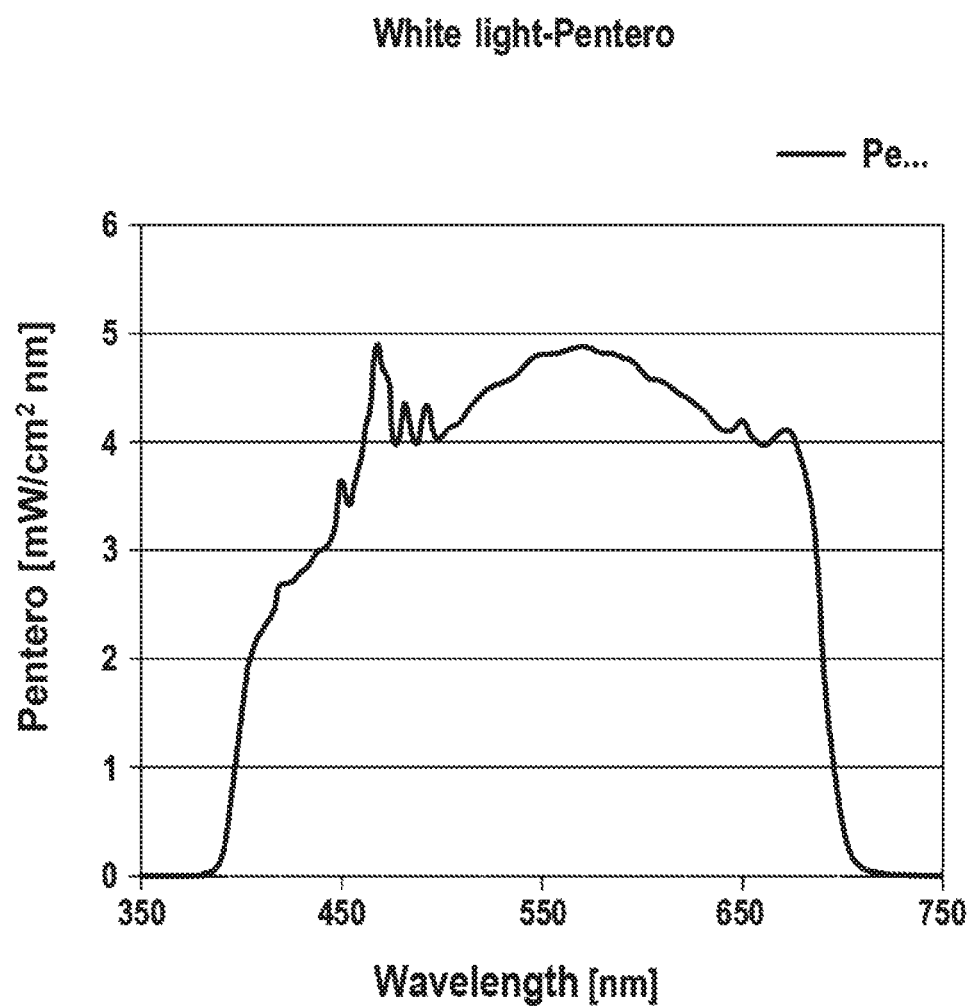
FIG. 4 shows the spectrum of a xenon light source of an operating microscope.

Since the respective color spectra or color temperatures of the light sources 2 and 4 differ, the xenon light source 2 of the operating microscope 1 having a color spectrum as imaged in FIG. 4 and the LED light source 4 of the endoscope 3 having a color spectrum as imaged in FIG. 3, there is a red tinge in the color impression as conveyed from the operating field 6 to the treating physician 5 through the operating microscope 1, the red tinge only being illustrated schematically by hatching in FIG. 2. This means that there is, at least in part, a color change as a result of the additional illumination by the LED light source 4 of the endoscope 3. This may lead to an impairment of the assessment of the operating field 6 by the treating physician 5. Here, the phrase "red tinge" should be understood in such a way that, at least subjectively, a color temperature that is too warm is discerned or perceived. Objectively, a white balance of a camera, for example of the operating microscope 1, exhibits a color deviation in the region of an operating field 6 that is illuminated together by the endoscope 3 and operating microscope 1, or their respective light sources 2, 4, and respectively observed accordingly. In particular, the light sources 2, 4 are matched to one another such that the color or the spectrum locus in the CIE (1931) color space is substantially not changed by the additional illumination of the operating field 6 by the light source 4 of the endoscope 3.

Figure 5:
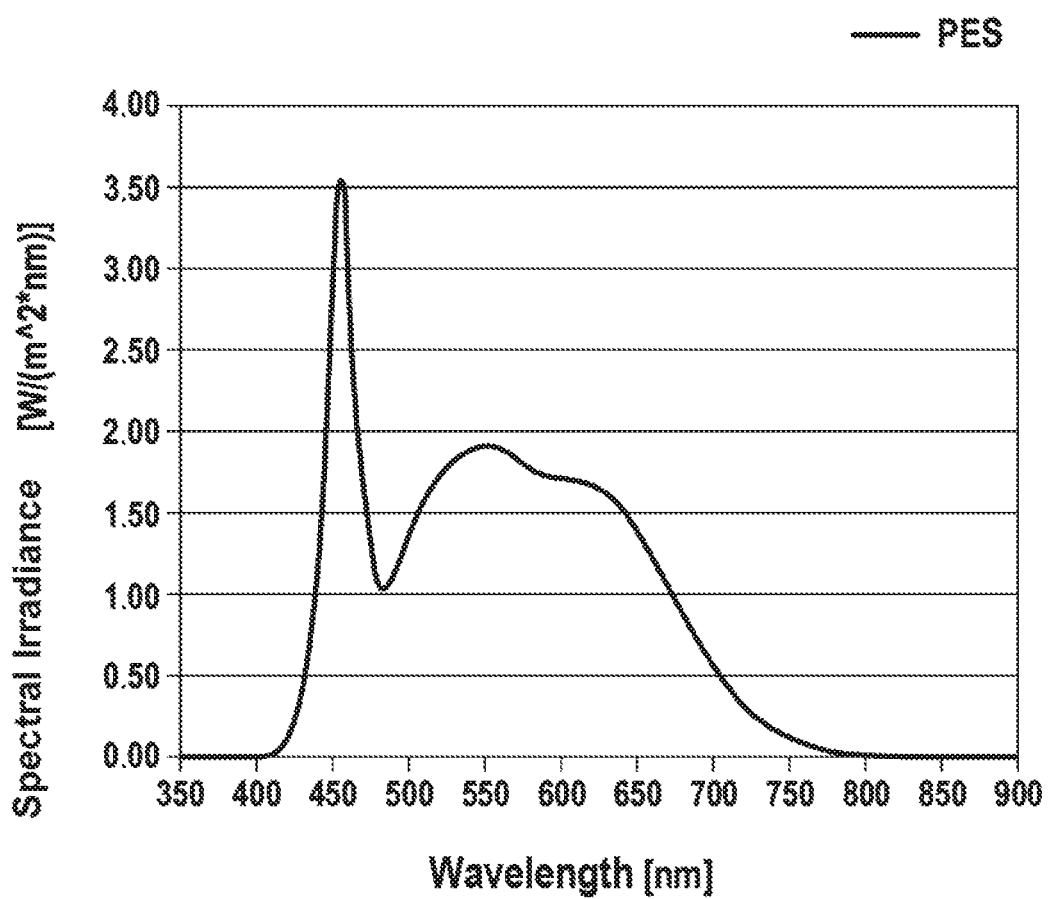
FIG. 5 shows the spectrum of an LED light source with a higher color temperature.

In the color spectra of different light sources 2, 4 illustrated in FIGS. 3 to 5, the wavelength in nanometers is specified along the x-axis in each case and the intensity in milliwatt per square centimeter and nanometer or watt per square meter and nanometer is specified along the y-axis in FIGS. 4 and 5 and an intensity in percent is specified along the y-axis in FIG. 3.

From the illustration in FIGS. 3 and 4, it is clearly visible that the light source 2 of the endoscope 1—see FIG. 3—has a substantially broader, uniformly distributed spectrum than an LED light source 4 of an endoscope 3 from FIG. 4. This brings about the red tinge, indicated by the hatching 10 in FIG. 2, in at least one region of the operating field 6.

If use is now made of an LED light source 4 with a color spectrum corresponding to FIG. 5 as an LED light source 4 of the endoscope 3, the red tinge or the white balance of a camera, see above, is substantially minimized. As a result of the increased white light component, the color impression of the operating field 6 through the operating microscope 1 is now only changed in a manner that is practically non-perceivable. Such an LED light source has a higher color temperature and can be selected depending on the employed light source 2 for the operating microscope 1.

In principle, it is also possible to modify a color temperature or intensity distribution of the LED light source 4 as desired by using RGB LEDs. An RGB LED can emit red, green and blue light with desired intensities. In principle, the light source 2 of the operating microscope may also include an LED.

Finally, color filters may also be provided in the illumination and/or observation beam paths 8, 9 of operating microscope 1 and/or endoscope in order to avoid a falsification of the color impression.

It is understood that the foregoing description is that of the exemplary embodiments of the invention and that various changes and modifications may be made thereto without departing from the spirit and scope of the invention as defined in the appended claims.

LIST OF REFERENCE NUMERALS

1 Operating microscope
2 Light source of 1
3 Endoscope
4 Light source of 3
5 Treating physician
6 Operating field
7 Combination of 1 and 3
8 Observation beam path of 1
9 Observation beam path of 3
10 Hatching for elucidating a red tinge

What is claimed is:

1. A system comprising:
an operating microscope including a first light source with a first color temperature, the first light source illuminating a first portion of an operating field; and
an endoscope including a second light source with a second color temperature, the second light source being a single LED and illuminating a second portion of the operating field,
wherein the single LED is configured such that the first and second color temperatures are matched to one another and such that an intensity distribution in a color spectrum of the first light source of the operating microscope substantially corresponds to the intensity distribution in the color spectrum of the second light source to prevent color differences in portions of the operating field that are illuminated and observed together by the operating microscope and the endoscope during at least one of optical imaging of the operating microscope, digital imaging of the operating microscope, optical imaging of the endoscope, or digital imaging of the endoscope.

2. The system of claim 1, wherein:
the first light source of the operating microscope is a xenon light source, and
the second color temperature of the second light source of the endoscope deviates from the first color temperature of the xenon light source of the operating microscope by at most 500 K.

3. The system of claim 1, wherein:
the first light source of the operating microscope is a xenon light source,
the second color temperature of the second light source of the endoscope deviates from the first color temperature of the xenon light source of the operating microscope by at most 300 K.

4. The system of claim 1, wherein:
the first light source of the operating microscope is a xenon light source, the operating microscope with the first light source has a first color rendering index and the endoscope with the second light source has a second color rendering index, and the first and second color rendering indices differ at most by a value of five.

5. The system of claim 1, wherein:

the first light source of the operating microscope is a xenon light source, the operating microscope with the first light source has a first color rendering index and the endoscope with the second light source has a second color rendering index, and the first and second color rendering indices differ at most by a value of four.

6. The system of claim 1, wherein:

the first light source of the operating microscope is a xenon light source, the operating microscope with the first light source has a first color rendering index and the endoscope with the second light source has a second color rendering index, and the first and second color rendering indices differ at most by a value of three.

7. The system of claim 1, wherein:

the first light source of the operating microscope is a xenon light source, the operating microscope with the first light source has a first color rendering index and the endoscope with the second light source has a second color rendering index, and the first and second color rendering indices differ at most by a value of two.

8. The system of claim 1, wherein:

the first light source of the operating microscope is a xenon light source, the operating microscope with the first light source has a first color rendering index and the endoscope with the second light source has a second color rendering index, and the first and second color rendering indices differ at most by a value of one.

9. The system of claim 1, wherein the endoscope is a portable endoscope.

10. The system of claim 9, wherein the second light source is integrated in the portable endoscope.

11. The system of claim 1, wherein the second light source of the endoscope is a white light LED.

12. The system of claim 1, wherein the second light source of the endoscope is an RGB LED.

13. The system of claim 1, wherein, within at least one of the optical imaging of the operating microscope, the digital imaging of the operating microscope, the optical imaging of the endoscope, or the digital imaging of the endoscope a white balance of at least one of a camera and the light source is performable.

14. The system of claim 1, wherein the operating microscope includes different light sources.

15. The system of claim 1, wherein, in at least one of the optical imaging of the operating microscope, the digital imaging of the microscope, the optical imaging of the endoscope, or the digital imaging of the endoscope an adaptation of a color temperature of a respective other light source is performable by image processing.

16. The system of claim 1, wherein the first and second color temperatures of the first light source and the second light source, respectively, are modifiable.

17. The system of claim 1, wherein color filters are individually assigned to the first light source and the second light source.

18. The system of claim 1, wherein color filters are assigned to both the first light source and the second light source.

* * * * *